US012594521B2

(12) United States Patent
Danville et al.

(10) Patent No.: US 12,594,521 B2
(45) Date of Patent: Apr. 7, 2026

(54) AUTOMATIC SPRAY DISPENSER

(71) Applicants: Robert C. Danville, Milton, GA (US);
Andrew G. Przyjemski, Somerville, MA (US)

(72) Inventors: Robert C. Danville, Milton, GA (US);
Andrew G. Przyjemski, Somerville, MA (US)

( * ) Notice: Subject to any disclaimer, the term of this patent is extended or adjusted under 35 U.S.C. 154(b) by 904 days.

(21) Appl. No.: 17/857,010

(22) Filed: Jul. 3, 2022

(65) Prior Publication Data

US 2024/0001280 A1 Jan. 4, 2024

(51) Int. Cl.
B01D 47/06 (2006.01)
G01N 33/00 (2006.01)

(52) U.S. Cl.
CPC ......... B01D 47/06 (2013.01); G01N 33/0004 (2013.01)

(58) Field of Classification Search
CPC ...... A61L 9/14; A61L 9/035; A61L 2209/111; B01D 47/06; G01N 33/0004
See application file for complete search history.

(56) References Cited

U.S. PATENT DOCUMENTS

| | | | |
|---|---|---|---|
| 9,939,412 B2 * | 4/2018 | Ichimura ............ | G01N 29/4418 |
| 2006/0210421 A1 * | 9/2006 | Hammond ................ | A61L 9/12 422/123 |
| 2015/0308993 A1 * | 10/2015 | Fukui ................. | G01N 30/8675 29/428 |

FOREIGN PATENT DOCUMENTS

DE 102009005203 A1 * 7/2010 ........... H03H 17/026

* cited by examiner

*Primary Examiner* — Jennifer Wecker
*Assistant Examiner* — Brady C Pilsbury

(57) ABSTRACT

The present invention relates to automatic odor treatment spray dispenser methods.

10 Claims, 10 Drawing Sheets

AUTOMATIC SPRAY DISPENSER

The present invention relates to automatic odor treatment spray dispensers.

BACKGROUND OF THE INVENTION

All patents, patent applications and other publications referred to herein are specifically incorporated herein by reference in their entirety.

There are many known odor causing agents that can be found at times in various closed environments such as homes, vehicles, workplaces, etc. By way of non-limiting example, such known odor causing agents include: 1,3-dimethylbenzene, 1-butene, 1-pentene, 1-propanethiol, 2,2-dimethylbutane, 2,4-dimethylpentane, 5,11,14,17-hexaoxaoctadecane, 2,5,11,14-pentaoxahexadecan-16-ol, 2,5,11,14-pentaoxapentadecane, 2,5-dimethylfuran, 2,5-dimethylhexane, 2-butanone (methyl ethyl ketone), 2-butene-1-thiol (crotyl), 2-furancarboxaldehyde, 2-methyl-1,3-buta-diene, 2-methyl-1-butene, 2-methyl-1-pentene, 2-methyl-1-propanethiol, 2-methyl-1-propene, 2-methyl-2-butene, 2-methylbutanal, 2-methylfuran, 2-methylhexane, 2-meth-ylpentane, 2-methylpropanal, 2-pentene, 2-propenylpropy-ldisulfide, 3-butene-1-thiol, 3-ethylenepyridine, 3-methyl-1-butanethiol, 3-methyl-2-pentene, 3-methylbutanal, 3-methylcyclopentene, 3-methylenepentane, 3-methylhep-tane, 3-methylpentane, 3-methylpyridine, acetaldehyde, acetone, allylmethyldisulfide, allylmethylsulfide (allyl mer-captan), ammonia, benzene, cis-1,3-dimethylcyclopentane, cyclohexane, cyclopentene, diallyidisulfide, dimethylsul-fide, dimethyldisulfide, dipropyldisulfide, ethanol, ethylben-zene, ethylene oxide, hexanal, hydrogen sulfide, isobutane, methanethiol, methyl mercaptan, methyl thiirane (methyl-ethylsulfide), methylcyclohexane, methylcyclopentane, n-heptane, n-hexane, n-octane, nonanal, pentanal, propanal, p-xylene, pyridine, pyrrole, styrene, toluene, 2,5,11,14,17-hexaoxaoctadecane, 2,5,11,14-pentaoxahexadecan-16-ol, 2-propenylpropyldisulfideacetone, and allylmethyldisulfide.

There are known odor causing agents that can be found at times in various bathroom environments. By way of non-limiting example, such known odor causing agents include: short-chain fatty acids such as propanoic acid, butanoic acid and pentanoic acid; organic and inorganic sulfur-containing molecules such as hydrogen sulfide, dimethyl sulfide, dim-ethyl disulfide, dimethyl trisulfide and methanethiol, benzo-pyrrole volatiles such as skatole and indole; organic and inorganic nitrogen-containing molecules such as ammonia and trimethylamine.

There are known devices and methods for reducing or remediating problems associated with objectionable odors from odor causing agents in environments. For example, 2010/0205731 A1 discloses a toilet freshener and a method for time-offset release of preparations in or on a toilet bowl. According to this reference, "It is therefore an object of the invention to provide a method and a device which provides optimized cleaning performance and/or fragrancing action in or on a toilet bowl." The device comprises a power source, control unit, sensor unit, a first container containing a first preparation, and at least one second container containing a second composition, wherein the power source, control unit, first container and at least the second container interact with a pump and/or a release element so that in at least two successive points in time $t_1$ and $t_2$ at least two different active substance preparations are released, wherein at least one active substance preparation is at least released into the interior of the toilet bowl. The control unit can include a programmable microprocessor in which there are preferably stored dispensing programs.

A basic control algorithm for controlling release of the preparations is shown, for example, in FIGS. 6-8. As shown, for example, in FIG. 6, sensor signals are received in the control unit wherein the received signal is compared to a threshold value stored within the control unit. [0156]. If the received signal exceeds the stored threshold value, the preparations are dispensed. U.S. Pat. No. 9,132,205 dis-closes an odor detection/abatement device comprising an airborne agent detector arranged to target the concentration of chemical compounds in the surrounding environment. Fragrances and odor abatement chemicals are dispensed into the environment using a wick. As stated at column 4, lines 49-56, Devices using chemical-specific, or odour-specific sen-sors for airborne contaminants have already been dis-closed. However, it has been realised that the cost of such devices and their sensitivity and accuracy or indeed their specificity is disadvantageous.

Therefore, in order to address that issue, it has been realised that a non-specific sensor (or sensors) that detects changes in the concentration of chemical con-taminants in the air, which chemicals are sensed as odours, fragrances and the like is a cost effective sensor(s) to use with a dispenser for air treatment agents.

And in column 7, lines 30-31 it states:

Advantages of the dispensing devices described above result from the use of a non-specific sensor.

Control means are provided for calculating an average of a predetermined "background "number of airborne agent lev-els, calculating a "current" airborne agent level, and dis-pensing at least one air treatment agent when the current airborne agent level exceeds the background airborne agent level by more than a predetermined amount (column 3, lines 47-56). "Preferably, the background airborne agent level and the current airborne agent level are temporally offset, pref-erably by at least 5 seconds, more preferably by at least 10 seconds, more preferably by at least 20 seconds" (column 4, lines 1-4). "The control means may be operable to calculate the deviation of the current airborne agent level from the background level by means of a subtraction of one from the other, and/or by means of a ratio of one to the other" (column 1, lines 45-49). US20060210421 also discloses an odor detection/abatement device comprising an airborne agent detector arranged to target the concentration of chemical compounds in the surrounding environment. According to this publication, an airborne agent detector comprises means to detect a threshold level or concentration of a target airborne agent wherein an air treatment agent is expelled upon detection of the airborne agent.

The present invention relates to a device and method for detecting target odor-causing airborne agent(s) and dispens-ing odor abatement spray in response thereto.

According to an embodiment, a device comprises
a. at least one sensor means for detecting the presence of at least one target odor causing agent in the surrounding environment and converting the response of each sen-sor means to an electrical output signal, wherein the electrical response of the sensor varies according to variations in the presence of the at least one target odor causing agent, b. processor means operationally connected to the sensor means for periodically collecting data points reflecting the electrical response of each electrically responsive sensor means, c. wherein a plurality of successive data points from each electrically responsive sensor means are processed to periodically estimate the slope of a line therethrough by linear least squares regression and to add the estimated slopes of all electrically responsive sensor means together, and d. spray means for spraying odor abatement fluid, the spray means being operationally connected to the processor means, e. wherein the spray means sprays odor abatement fluid when the added slopes of all sensor means exceeds a threshold level.

According to another embodiment a method comprises:

a. exposing at least one sensor means to a surrounding environment for detecting and responding to the presence of at least one odor causing agent, b. periodically converting the response of each sensor means to a periodic electrical output signal, c. sending each periodic electrical output signal to control means wherein a plurality of periodic electrical output signals are used to calculate by linear least squares regression the slope between the periodic electrical output signals, d. adding the slopes e. activating expulsion of an odor treatment agent into the surrounding environment when the added slopes of all sensor means exceeds a threshold level.

In the context of the prior art, the use of linear least squares regression in accordance with the present invention is considered to provide improved accuracy and operation of these devices.

In addition, while the use of inexpensive, non-specific odor sensor means may be desirable, the accuracy of the same can vary significantly within a group of the same sensor. Thus, the use of such non-specific sensor means in a number of devices should necessitate the calibration of each device to compensate for the inconsistencies. The use of linear least squares regression in accordance with the present invention can eliminate the need for such repetitive calibrations. Once the first sensor means is calibrated in a device it should not be necessary to calibrate subsequent uses of the same sensor in subsequent devices.

DETAILED DESCRIPTION OF THE INVENTION

Figure 1:
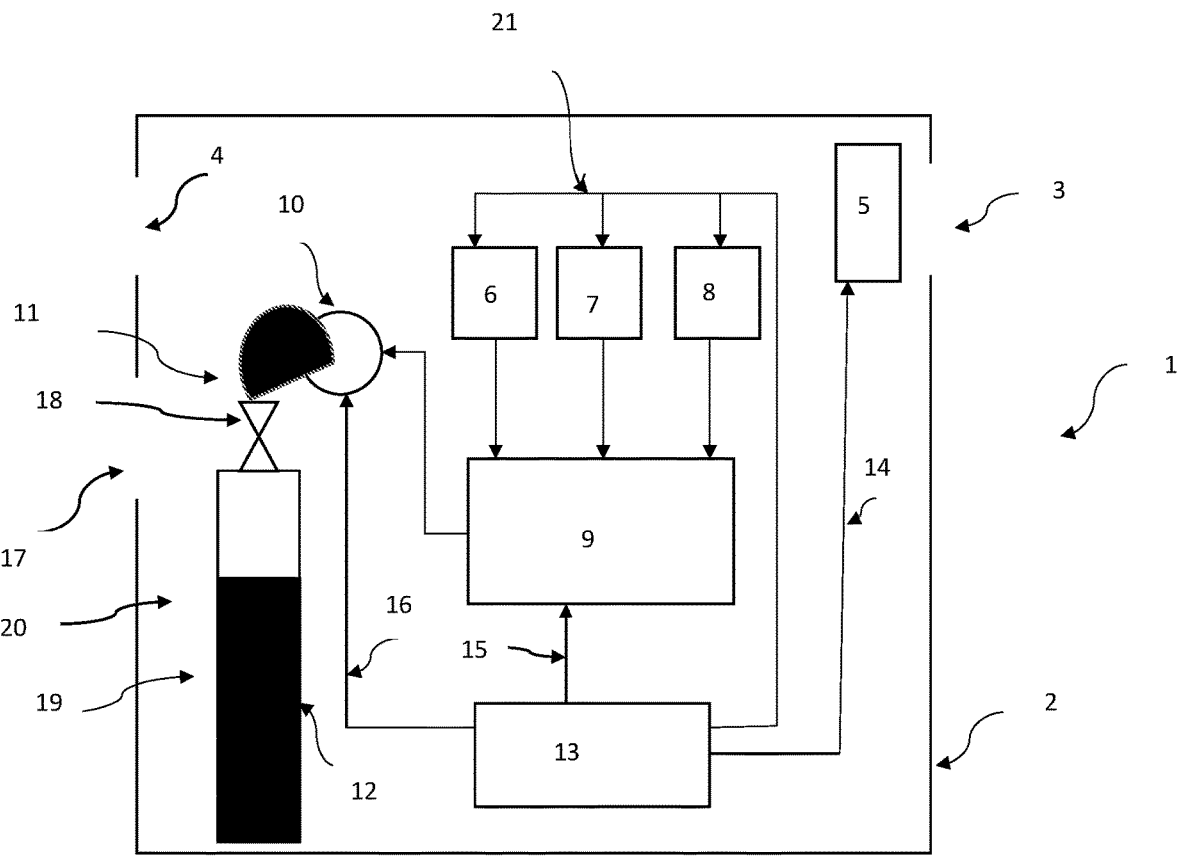
FIG. 1 is a schematic diagram illustrating a non-limiting example of an odor detection device according to the present invention.

In the following detailed description, reference is made to the accompanying drawings, which form a part hereof. The illustrative embodiments described in the detailed description, drawings, and claims are not meant to be limiting. Other embodiments may be utilized, and other changes may be made, without departing from the spirit or scope of the subject matter presented herein.

All publications, patents and patent applications cited herein, whether supra or infra, are hereby incorporated herein by reference in their entirety to the same extent as if each individual publication, patent or patent application was specifically and individually indicated to be incorporated herein by reference. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, as well as, any range formed within a specified range, regardless of whether ranges are separately disclosed. Where a range of numerical values is recited herein, unless otherwise stated, the range is intended to include the endpoints thereof, and all integers and fractions within the range. For example, recitation of 1-5 is intended to include all integers including and between 1 and 5 and all fractions and decimals between 1 and 5, e.g., 1, 1.1, 1.2, 1.3 etc. Furthermore, when a list of specific number is provided, unless otherwise stated, it is intended to include any range between and including the upper and lower limits. For example, a list of numbers such as 1, 2, 3, 4, 5, and 6 is intended to include the range of 2-5. It is not intended that the scope of the invention be limited to the specific values recited when defining a specific range. Similarly, recitation of at least about or up to about a number is intended to include that number and all integers, fractions and decimals greater than or up to that number as indicated. For example, at least 5 is intended to include 5 and all fractions and decimals above 5, e.g., 5.1, 5.2, 5.3 etc.

It is noted that, as used in this specification and the appended claims, the singular forms "a," "an" and "the" include plural referents unless the content clearly dictates otherwise. Unless otherwise expressly indicated herein, all amounts are based on volume.

According to an embodiment, a device comprises:

a. at least one sensor means for detecting the presence of at least one target odor causing agent in the surrounding environment and converting the response of each sensor means to an electrical output signal, wherein the electrical response of the sensor varies according to variations in the presence of the at least one target odor causing agent, b. processor means operationally connected to the sensor means for periodically collecting data points reflecting the electrical response of each electrically responsive sensor means, c. wherein a plurality of successive data points from each electrically responsive sensor means are processed to periodically estimate the slope of a line therethrough by linear least squares regression and to add the estimated slopes of all electrically responsive sensor means together, and d. spray means for spraying odor abatement fluid, the spray means being operationally connected to the processor means, e. wherein the spray means sprays odor abatement fluid when the added slopes of all sensor means exceeds a threshold level.

With reference to FIG. 1 of the drawings, 1 generally refers to a schematic of an illustrative odor detection device comprised of an outside housing 2 having an air inlet 3 and an air outlet 4. This device is placed in a surrounding environment such as a room in a house (such as a bathroom), in a vehicle or anywhere else where it is desirable to treat for objectionable odors, for example in a public bathroom. As shown in FIG. 1 for illustrative purposes, three sensor means 6, 7, and 8 are provided within housing 2. It is possible to use fewer sensor means with each being specific to a specific target odor gas, for example, sensor means 6 could be specific to detect ammonia only and sensor means 7 to detect hydrogen sulfide. While at least one sensor means is possible, as shown in FIG. 1, three sensor means are illustrated. When using plural sensor means, there may be some overlap in the target odor gases detected. Preferably each sensor means detects at least one target odor gas that the others do not. By way of a non-limiting illustrative example, sensor means 6 could detect ammonia and possibly other gases excluding hydrogen sulfide, sensor means 7 could detect hydrogen sulfide and possibly other gases excluding ammonia, and sensor means 8 could detect volatile organics but not ammonia or hydrogen sulfide. Such a "non-specific" arrangement allows for the use of cheaper, non-specific sensor means.

Any known odor gas sensor means capable of detecting the target odor gases is suitable for use. By way of nonlimiting illustrative example, metal oxide semiconductor type gas sensors are well known and commonly used. Based on the concentration of the target odor gas the gas sensor means produces a corresponding potential difference by changing the resistance of the material inside the sensor, which can be measured as output voltage. Based on this voltage value the type and relative concentration of the gas can be estimated. As is known, gas sensor means typically consist of a gas sensing layer, a heater coil, an electrode line, a ceramic and an electrode.

The gas sensing layer is typically a membrane that only allows specific target gases to pass therethrough which increases the conductivity with increasing concentration. This layer changes its resistance based on changes in the concentration of the target gas(es) in the environment. It is known that semi-conducting metal oxide (MOX) sensors can exhibit strong sensitivity to traces of reactive gases present in the air. Amongst the known oxides which are used as MOX sensors are tin dioxide ($SnO_2$). The $SnO_2$ sensors can be enhanced, selectivity-wise and sensitivity-wise by the use of catalytic additives, such as the Pt. $SnO_2$ has excess electrons (donor element). The resistance change induced by the sensors is caused by loss or gain of the surface electrons as a result of absorbed oxygen reacting with a target gas. So whenever target gas(es) are being detected the resistance of the layer changes and the current flown through it varies which represents the change in concentration of the gases.

It is known that heated semi-conducting MOX exhibits strong sensitivity to traces of reactive gases present in the air. The purpose of the heater coil is to heat the sensing element so that the sensitivity and efficiency of the sensing element increases. It can be made, for example, of Nickel-Chromium or Tantalum/Platinum which has a high melting point so that it can stay heated up without getting melted. The electrode line carries the output current from the sensor(s). It is typical to use platinum wires due to their high conductor efficiency. Ceramic is placed between the heater coil and the gas sensing layer to maintain the heating of the gas sensing layer. The ceramic is typically made of aluminum oxide. The electrode is a junction between the sensing layer and the electrode line to provide for the flow of output current from the sensor to a terminal. By way of non-limiting example, while the electrode can be made of any good conductor material, e.g., Gold as this material is an excellent conductor. Numeral 5 in FIG. 1 refers to fan means for moving air through the device from inlet 3, across the sensor means and out through exit 4. Location of the fan means within the housing is not critical as long as it provides for the noted flow of air across the sensor means and doesn't interfere with effective flow of spray from spray means 20. Fan means 5 can operate continuously or can be programmed to operate intermittently.

Container means 12 is provided to contain an odor abatement fluid 19 for treating target odor gases. Container means 12 can be any suitable receptacle such as a canister or bottle. The abatement fluid can assume any useable form such as pumpable liquid or a pressurized liquid-gas mixture. Odor abatement fluid can be dispensed via outlet 17 from nozzle means 18 as an aerosol, for example, by pumping of liquid or valve release of the pressurized liquid gas mixture.

Known driver means 10 is provided to move mechanical arm 11. Driver means 10 can be, for example, a servo motor designed to impart the desired movement to mechanical arm 11. By way of non-limiting example, in the instance that container means 12 contains pumpable liquid, driver means moves mechanical arm up and down with a regular frequency to impart a pumping motion to nozzle means 18. In the instance that container means contains pressurized liquid-gas mixture, driver means moves mechanical arm 11 down for the desired period to dispense aerosol and is then moved upwardly away from nozzle means 18. The spray means may continue to spray the odor abatement fluid until the device no longer detects a threshold level of the added slopes of all sensor means. Alternatively, the device may be programmed to spray the odor abatement fluid for a preset time once the device detects a threshold level of the added slopes of all sensor means.

Reference numeral 13 generally refers to a known power source which can take the form, for example, of replaceable or rechargeable batteries, solar cells, or direct electricity provided by an electrical outlet. Power source 13 provides energy to all components requiring the same, as shown, at 14 to fan means 5, at 15 to control unit 9, at 16 to driver means 10 and at 21 to sensor means 6, 7, and 8.

Control means 9 is provided such as a conventional microcontroller, which includes processor means such as a microprocessor for executing a program stored in internal memory. The memory also provides storage locations for data required for odor sensor and abatement operation. The control means 9 has input/output circuits for interfacing to external components. As an alternative to a programmable means, a control circuit can be implemented by a custom integrated circuit that has logic circuitry for controlling operation of the odor sensor and abatement device.

According to another aspect, a plurality of sensor means is provided, wherein each sensor means detects (responds to) a different target gas. According to a further aspect, a first sensor means targets sulfide target gases and other gases excluding fragrance gases and a second sensor means senses total organic volatiles excluding sulfide target gases. According to still a further aspect, a first sensor means targets sulfide target gases and other gases excluding fragrance gases and ammonia, a second sensor means senses total organic volatiles excluding sulfide target gases and ammonia target gases, and a third sensor means senses ammonia target gases and other gases excluding sulfide target gases and fragrance gases.

Fragrance (gases) are known for adding a pleasant aroma to the environment. Non-limiting illustrative examples of fragrances, for example those illustrated in US20060223738 AI, are the synthetic products of the ester, ether, aldehyde, ketone, alcohol and hydrocarbon type. Odorant compounds of the ester type are, for example, benzyl acetate, phenoxy-ethyl isobutyrate, p-tert-butylcyclohexyl acetate, linalyl acetate, dimethylbenzylcarbinyl acetate, phenylethyl acetate, linalyl benzoate, benzyl formate, ethyl methyl phe-nylglycinate, allyl cyclohexylpropionate, styrallyl propi-onate and benzyl salicylate. The ethers include, for example, benzyl ethyl ether; the aldehydes include, for example, the linear alkanals having 8-I8 carbon atoms, citral, citronellal, citronellyloxyacetaldehyde, cyclamen aldehyde, hydroxycitronellal, lilial and bourgeonal; the ketones include, for example, the ionones, a-isomethylionone and methyl cedryl ketone; the alcohols include anethole, citro-nellol, eugenol, geraniol, linalool, phenylethyl alcohol and terpineol; the hydrocarbons include primarily the terpenes such as limonene and pinene. Mixtures of fragrances which together produce a pleasing fragrance note can also be used. Such fragrance oils may also comprise natural odorant mixtures, as are obtainable from vegetable sources, for example pine oil, citrus oil, jasmine oil, patchouli oil, rose oil or ylang-ylang oil. Likewise, are muscatel, sage oil, chamomile oil, clove oil, balm oil, mint oil, cinnamon leaf oil, lime blossom oil, juniper berry oil, vetiver oil, olibanum oil, galbanum oil and labdanum oil, and also orange blossom oil, neroli oil, orange peel oil and sandalwood oil.

According to a further aspect, devices in accordance with the present invention may include a wireless local area network module capable of communicating with other devices via known communications for example IEEE stan-dards such as WiFi, Zigbee, bluetooth, etc. By way of example, communications protocols could include one or more of Zigbee, MiFi, MiWi, DMX, ANT, Z-Wave, Insteon, JenNet-IP, X10, mesh network, visible light, ultrasound, infrared light, and IP version 6 (IPv6), such as IPv6 over Low Power Wireless Personal Area Networks.

These devices could be operated either directly by pushbut-ton or by a signal from a network or remote-control device, e.g., a cell phone or computer.

As already noted, a plurality of data points is processed by each sensor means. For example, at least 3, or at least 5, or at least 10, at least 15 or at least 20 data points can be processed by each sensor means. Also as already noted the processor means are operationally connected to the sensor means for periodically collecting and processing data points reflecting the electrical response of each electrically respon-sive sensor means. Any period $(t_0, t_1)$ for collecting the data points can be used. For example, data points can be collected at least every second (where $t_1=1$), or at least every 3 seconds (where $t_1=3$), or at least every 5 seconds (where $t_1=5$), or at least every 10 seconds (where $t_1=10$).

The Algorithms

According to one aspect, the algorithms utilize linear least square regression, optional data conditioning, optional data normalization, and data weighting. The purpose of the algorithms is to determine when to spray odor abatement fluid. The goal is to spray the product when a bad odor is present, and inversely, not spray the product when no odor is present. Accordingly, there are two machine states: spray-ing (bad odor present), or not spraying (no odor present). A variable with only two states is called a Boolean and has two possible variables: true (1) and false (0). From here on true will be referred as 1 and false will be referred as 0. The goal of the algorithms is to receive sensor data, interpret it, and return either a '0' (don't spray) or a '1' (do spray). If programmed correctly, the system should return a 0 when there is no bad odor present, and a 1 when there is a bad odor present.

Linear Least Squares Regression

As noted, according to an aspect, a plurality of successive data points from each electrically responsive sensor means are processed to periodically estimate the slope of a line therethrough by linear least squares regression Since data collected and plotted on a 2-dimensional graph will typically not lie on a straight line, linear least square regression is utilized to estimate a straight line through the data.

Estimating a straight line from given data uses the for-mula:

$$y=mx+b \tag{1}$$

Where m is the slope and b is the y intercept. For the purpose of performing linear least squares regression:

$$m = \frac{\Sigma(x - x_{ave}) \times (y - Y_{ave})}{\Sigma(x - x_{ave})^2} \tag{2}$$

where $x_{ave}$ denotes the average of the x values and $y_{ave}$ denotes the average of the y values. Then, b can be solved for by substituting in corresponding values for $y_{ave}$ and $x_{ave}$ in equation (1)

Following is an illustration of the application of linear least squares regression to hypothetical processed data points measured at 2 second intervals.

| Hypothetical Raw Data | | | | | | | |
|---|---|---|---|---|---|---|---|
| x (time) (seconds) | y (sensor measurement) | $x_{ave}$ | $y_{ave}$ | $x - x_{ave}$ | $y - y_{ave}$ | $(x - x_{ave}) \times (y - y_{ave})$ | $(x - x_{ave})^2$ |
| 1 | 14 | 4 | 19.75 | −3 | −5.75 | 17.25 | 9 |
| 3 | 16 | | | −1 | −3.75 | 3.75 | 1 |
| 5 | 22 | | | 1 | 2.25 | 2.25 | 1 |
| 7 | 27 | | | 3 | 7.25 | 21.75 | 9 |

According to equation (2)

$$m = \frac{\Sigma(x - x_{ave}) \times (y - Y_{ave})}{\Sigma(x - x_{ave})^2}$$

$$m = \frac{45}{20} = 2.25$$

solving for b according to equation (1):

$$b = y_{ave} - m x_{ave}$$

$$b = 19.75 - 2.25(4) = 10.75$$

and y is determined by:

$$y = m x_{ave} + b$$

Accordingly, $$y = 2.25 x_{ave} + 10.75$$

Now, starting at $t_0$ (x=0), and adding 1 second increments to equation (3):

| $x_{ave}$ | y |
|---|---|
| 0 | 10.75 |
| 1 | 13 |
| 2 | 15.25 |
| 3 | 17.5 |
| 4 | 19.75 |
| 5 | 22 |
| 6 | 24.25 |
| 7 | 26.5 |
| 8 | 28.75 |

Figure 7:
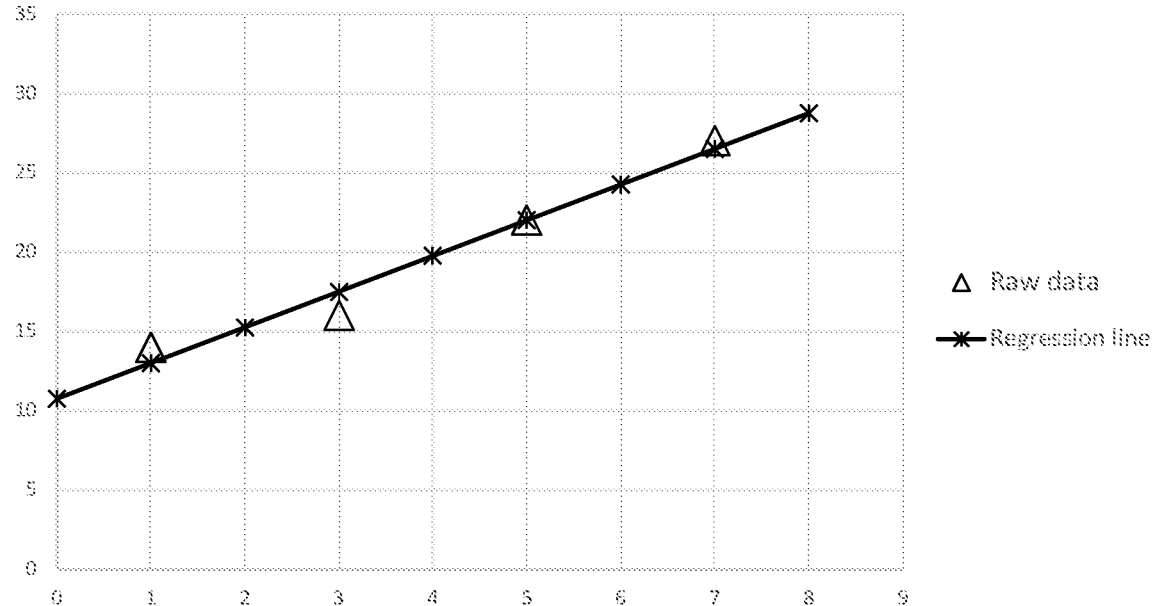
FIG. 7 is a plot of time vs. regression line data.

Plotting time vs. regression line data and the raw data on the same graph is shown in FIG. 7: However, according to one aspect, the y intercept b is removed from the equation due to the variability between sensors and the preference not to attempt to calibrate each one.

According to one aspect, linear least squares regression is continuously applied to a set of data from each sensor means collected over a specified time segment. i.e., "moving linear least squares regression". Moving linear least squares regression refers to the temporal resolution of the data processing method. Similar to a moving average, a window consisting of a predetermined set of data contains the most recent values collected by a given sensor means. When a new data value is provided by the sensor means to the processor, the data stored within the window shifts, discarding the oldest value in the window and storing the newest value. It is by this method that a linear regression line can be fit to a new set of data upon each time cycle, or upon receiving a new sensor value.

Optional Data Conditioning

According to another aspect, the data optionally is subjected to data conditioning. A given target odor sensor means records data on a range determined by the design of said sensor means. For example, this range could be voltage based or count based. By way of example, voltage-based sensor means may return a voltage between zero and five volts, and count based sensor means may return a measurement of airborne particulates with units of parts per million (ppm) or parts per billion (ppb). Thus, different data ranges could result in making it difficult to plot the data on the same graph. To allow for comparison of such sensor means with different units, it may be necessary to scale the data obtained from a plurality of sensor means. By way of illustration, data conditioning as used herein follows unity-based normalization to bring the range of values for a given sensor to a desired range, e.g., [0,1]. The following equation details the unity-based approach for conditioning a set of data.

$$x' = \frac{x - x_{min}}{x_{max} - x_{min}} \tag{3}$$

where $x_{min}$ and $x_{max}$ are unique to each sensor, and x' is the conditioned data.

Following is an illustration of the application of data conditioning to hypothetical processed data points measured at 2 second intervals using y as the measured values instead of x.

| | | | | | | Hypothetical Raw Data | | |
|---|---|---|---|---|---|---|---|---|
| x (time) (seconds) | y (sensor measurement) | $x_{ave}$ | $y_{ave}$ | $x - x_{ave}$ | $y - y_{ave}$ | $(x - x_{ave}) \times (y - y_{ave})$ | $(x - x_{ave})^2$ | |
| 1 | 14 | 4 | 19.75 | −3 | −5.75 | 17.25 | 9 | |
| 3 | 16 | | | −1 | −3.75 | 3.75 | 1 | |
| 5 | 22 | | | 1 | 2.25 | 2.25 | 1 | |
| 7 | 27 | | | 3 | 7.25 | 21.75 | 9 | |

In this instance substituting y for the x values in equation (3):

$$y_{max} = 27$$

$$y_{min} = 14$$

| Conditioned Data | | |
|---|---|---|
| x (time) (seconds) | y (sensor measurement) | y' |
| 1 | 14 | 0 |
| 3 | 16 | .15 |
| 5 | 22 | .62 |
| 7 | 27 | 1.0 |

According to a further aspect, the slopes are optionally normalized. The slopes calculated according to equation (2) can, by way of non-limiting illustrative example, be normalized to the range [−1,1] using the following equation:

$$m' = 2\frac{m - m_{min}}{m_{max} - m_{min}} - 1 \quad (4)$$

where $m_{min} = -m_{max}$. Therefore, equation (5) can be simplified to:

$$m' = \frac{m}{m_{max}} \quad (5)$$

where $m_{max}$ is a function of the temporal resolution of the linear regression analysis and the maximum sensor means value. As previously noted, each regression line is calculated over $[t_0, t_1]$ and the maximum sensor means value is exactly equal to one after unity-based conditioning as explained above. Therefore, $m_{max}$ can be defined as:

$$m_{max} = \frac{1}{t_1 - t_0} = (t_1 - t_0)^{-1} \quad (6)$$

By substitution we get the normalized slope as:

$$m' = m(t_1 - t_0) \quad (7)$$

Odor Determination

According to another aspect, the respective slopes are weighted before being added together. The slopes thus determined as above are weighted using weighting constants and used to return a value correlating to the probability that target odor causing agent is present sufficiently to likely cause the sensation of a foul odor and can be determined by:

$$\beta_1 m_1 + \beta_2 m_2 + \ldots \beta_p m_p = x \quad (8)$$

where p is the number of sensor means being used and $\beta_p$ is a predetermined weighting constant associated with each sensor means. The value of x is then used to render a Boolean value that dictates whether the spray means are to be activated according to:

$$f(x) = \begin{cases} 0 & x \le 1 \\ 1 & 1 < x \end{cases} \quad (9)$$

A value less than or equal to 1 dictates that the spray means should not be activated, while a value greater than 1 dictates that the spray means should be activated.

Determination of the Sensor Means Weighting Constants

Different values of $\beta$ are used on a data set until a function is found that most accurately predicts the presence of a bad odor. Each $\beta$ value is set such that the error of equation (9) is minimized. Initially, equation (9) returns a 'guess' as to whether or not an odor is present, given a set of data from a plurality of sensor means. Whether equation (9) returns an accurate response or not can be determined by comparing the result of equation (9) against a "ground truth data set". As used herein, a "ground truth data set" is defined as the correct values that equation (9) is designed to return. In this context, a ground truth data set consists of qualitative human assessments as to whether a foul odor is present or not in the environment in which the odor sensing device is placed. This "ground truth data set" is paired with sensor data collected during the same time frame to create a labeled training data set.

Using this training data, a set of $\beta$ values are found that minimize the error of equation (9). These $\beta$ values are found using the known algorithmic tool of gradient descent, in this instance gradient descent for multiple variables This process will produce an inferred function that can then be applied to unseen data to produce responses as accurate as possible. This process is known as supervised machine learning and serves as the basis for the inferred function.

Gradient Descent

Gradient Descent is a known iterative optimization algorithm used in training a model. In simple words, Gradient Descent finds the parameters that minimize the cost function (error in prediction). Gradient Descent does this by iteratively moving toward a set of parameter values that minimize the cost function, taking steps in the opposite direction of the gradient.

The cost function is the method by which the algorithm determines the accuracy of the inferred function. The cost function in this application is the equation for the Matthews Correlation Coefficient (MCC) which is commonly used in machine learning as a measure of the quality of binary classifications. In this application the determination of whether an odor is present or not can be considered a binary system. The Matthews Correlation Coefficient returns a value between $-1$ and $+1$. A value of $+1$ represents a perfect prediction, 0 represents random chance, and $-1$ represents total disagreement between prediction and observation. In this application, minimizing the cost function corresponds with obtaining a MCC value as close to $+1$ as possible.

$$MCC = \frac{TP \times TN - FP \times FN}{\sqrt{(TP + FP)(TP + FN)(TN + FP)(TN + FN)}} \quad (10)$$

Where TP is the total number of true positives over a training data set, TN is the total number of true negatives over a training data set, FP is the total number of false positives over a training data set, and FN is the total number of false negatives over a training data set. A true positive is defined as a predicted positive value when the observed value is also positive. A true negative is defined as a predicted negative value when the observed value is also negative. A false positive is defined as a predicted positive value when the observed value is negative. A false negative is defined as a predicted negative value when the observed value is positive.

Using equation (10) the accuracy of the inferred function over a set of training data can be determined. Knowing the accuracy of the inferred function will accommodate minimization of the error in the process known as gradient descent.

Before the gradient descent process is begun, a set of initial Beta values are selected. The initial value of each Beta is not critical as the gradient descent process will refine these values into something more precise. By way of non-limiting example, the initial Beta values can be some value in the range of $[-20,20]$. The next step is to define a learning rate factor. The learning rate designates how fast the Beta values will change during the descent process. Usually a high learning rate will result in better computational efficiency at the cost of accuracy, while a low learning rate will result in higher accuracy at the cost of computational efficiency. By way of non-limiting example, a process a learning rate in the range of $[0.0001,1]$ is selected.

To begin the gradient descent process, the initial set of Beta values selected in the inferred function are used to calculate an MCC value for the given set of training data. Next an array of new Beta values is created that consists of all the different combinations of the original Beta values+/−the learning rate factor. For example, if there are three Beta values and each equal 1 with a learning rate of 0.1, the array will be the result shown in the following table.

| Beta Value Array | | |
|---|---|---|
| Beta1 | Beta2 | Beta3 |
| 0.9 | 0.9 | 0.9 |
| 1 | 0.9 | 0.9 |
| 1.1 | 0.9 | 0.9 |
| 0.9 | 1 | 0.9 |
| 1 | 1 | 0.9 |
| 1.1 | 1 | 0.9 |
| 0.9 | 1.1 | 0.9 |
| 1 | 1.1 | 0.9 |
| 1.1 | 1.1 | 0.9 |
| 0.9 | 0.9 | 1 |
| 1 | 0.9 | 1 |
| 1.1 | 0.9 | 1 |
| 0.9 | 1 | 1 |
| 1 | 1 | 1 |
| 1.1 | 1 | 1 |
| 0.9 | 1.1 | 1 |
| 1 | 1.1 | 1 |
| 1.1 | 1.1 | 1 |
| 0.9 | 0.9 | 1.1 |
| 1 | 0.9 | 1.1 |
| 1.1 | 0.9 | 1.1 |
| 0.9 | 1 | 1.1 |
| 1 | 1 | 1.1 |
| 1.1 | 1 | 1.1 |
| 0.9 | 1.1 | 1.1 |
| 1 | 1.1 | 1.1 |
| 1.1 | 1.1 | 1.1 |

The above table consists of all combinations of either the original Beta values, the original Beta values plus the learning rate factor, or the original Beta values minus the learning rate factor. Each row of Beta factors in this table are then used with the inferred function to calculate an MCC value over the training data set. This yields an MCC value for each row, similarly to the above Value Array table, shown below.

| Beta Array with MCC Values | | | |
|---|---|---|---|
| Beta1 | Beta2 | Beta3 | MCC |
| 0.9 | 0.9 | 0.9 | −0.32 |
| 1 | 0.9 | 0.9 | −0.08 |
| 1.1 | 0.9 | 0.9 | −0.09 |
| 0.9 | 1 | 0.9 | −0.94 |
| 1 | 1 | 0.9 | 0.13 |
| 1.1 | 1 | 0.9 | −0.88 |
| 0.9 | 1.1 | 0.9 | 0.13 |
| 1 | 1.1 | 0.9 | 0.22 |
| 1.1 | 1.1 | 0.9 | −0.98 |
| 0.9 | 0.9 | 1 | −0.23 |
| 1 | 0.9 | 1 | −0.73 |
| 1.1 | 0.9 | 1 | 0.57 |
| 0.9 | 1 | 1 | −0.29 |
| 1 | 1 | 1 | 0.10 |
| 1.1 | 1 | 1 | −0.20 |
| 0.9 | 1.1 | 1 | −0.42 |
| 1 | 1.1 | 1 | −0.78 |
| 1.1 | 1.1 | 1 | −0.25 |
| 0.9 | 0.9 | 1.1 | 0.45 |
| 1 | 0.9 | 1.1 | 0.42 |
| 1.1 | 0.9 | 1.1 | 0.14 |
| 0.9 | 1 | 1.1 | −0.77 |
| 1 | 1 | 1.1 | −0.24 |

-continued

| Beta Array with MCC Values | | | |
|---|---|---|---|
| Beta1 | Beta2 | Beta3 | MCC |
| 1.1 | 1 | 1.1 | 0.48 |
| 0.9 | 1.1 | 1.1 | 0.33 |
| 1 | 1.1 | 1.1 | 0.29 |
| 1.1 | 1.1 | 1.1 | 0.70 |

It can be seen in the above table that the MCC value associated with the initial Beta values of (1, 1, 1) is 0.10. Since the goal is to obtain an MCC value as close to 1 as possible the direction of greatest positive gradient is the set of Beta values that are closest to 1. Which in the case of the above table is that last row of Beta values that produce an MCC value of 0.70.

The process detailed above is now repeated with initial Beta values of (1.1, 1.1, 1.1), and repeated until the exit condition is met. The exit condition is met if the newly determined MCC value is almost exactly equal to the previously determined MCC value, (for example on the order of $10^{-3}$ to prevent the function from looping indefinitely). The idea is that if the change in MCC value from one iteration to the next is less than epsilon, then the gradient descent process has found a value that is significantly close to the local maximum, therefore the gradient descent process can be ended. Performing this process iteratively will result in new Beta values that represent the highest MCC value (closest to +1) that can be achieved over the given training data set. These Beta values are then used to finalize the inferred function.

Figure 6:
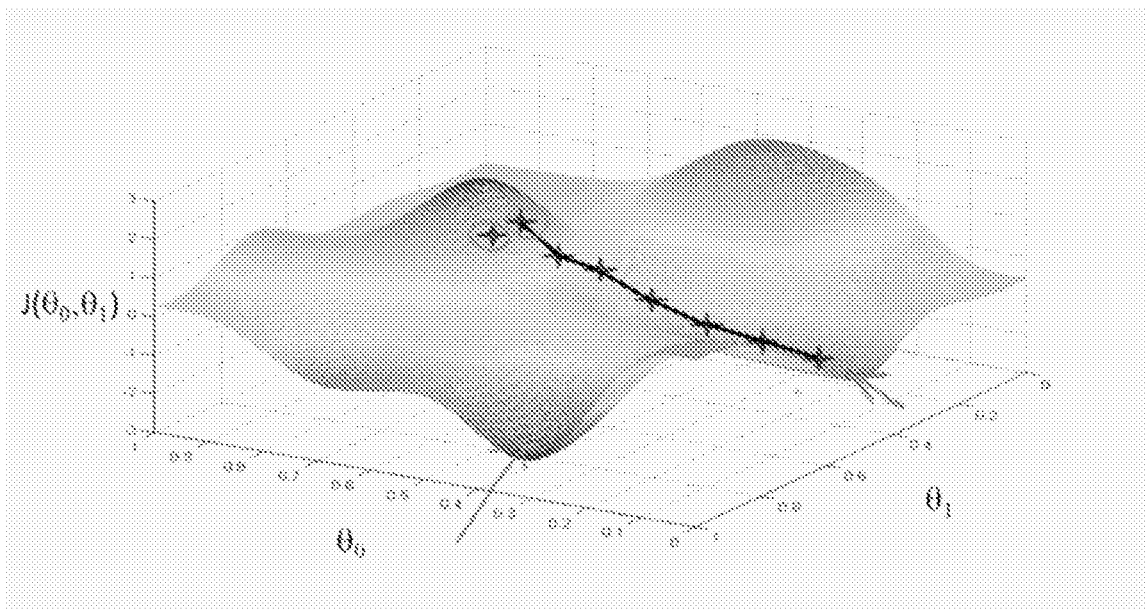
FIG. 6 is a representation of gradient descent used to reduce error in the cost function showing a path from an area of high error to a local minimum where error is minimized

FIG. 6 is a good visual representation of how gradient descent is used to reduce error in the cost function. It shows the path from an area of high error to a local minimum where error is minimized.

EXAMPLES

The following Examples are provided to illustrate certain aspects of the invention, and are not intended to limit the scope thereof.

Gradient descent for multiple variables is a well-known mathematical approach, as illustrated, by way of non-limiting example, at http://mlwiki.org/index.php/Gradient_Descent which is substantially reproduced below:

Gradient Descent

Suppose we have a cost function JJ and want to minimize it say it takes 2 parameters $\theta_0$ and $\theta_1$ So we have $J(\theta_0, \theta_1)$ which we want to minimize Idea:

start with some $(\theta_0, \theta_1)$ say (0,0)

keep changing $(\theta_0, \theta_1)$ to reduce $J(\theta_0, \theta_1)$ until we end up at a minimum In the pseudo code repeat until convergence ○ for $j = 0$ and $j = 1$ ○ $\theta_j = \theta_j - \alpha \dfrac{\partial}{\partial \theta_i} J(\theta_0, \theta_1)$ $\alpha$ is the learning rate, value that specifies the size of the steps we take Simultaneous Update Note that the update for ($\theta_0$, $\theta_1$) must be simultaneous. That is

- $\tau_0 = \theta_0 - \alpha \frac{\partial}{\partial \theta_0} J(\theta_0, \theta_1)$

- $\tau_1 = \theta_1 - \alpha \frac{\partial}{\partial \theta_1} J(\theta_0, \theta_1)$

- $\theta_0 = \tau_0$

- $\theta_1 = \tau_1$

As you see, $\theta_0$ is used to calculate new value for $\theta_1$, so we cannot update it before we calculate new value for $\theta_0$.

This is called simultaneous update

Intuition

Figure 8:
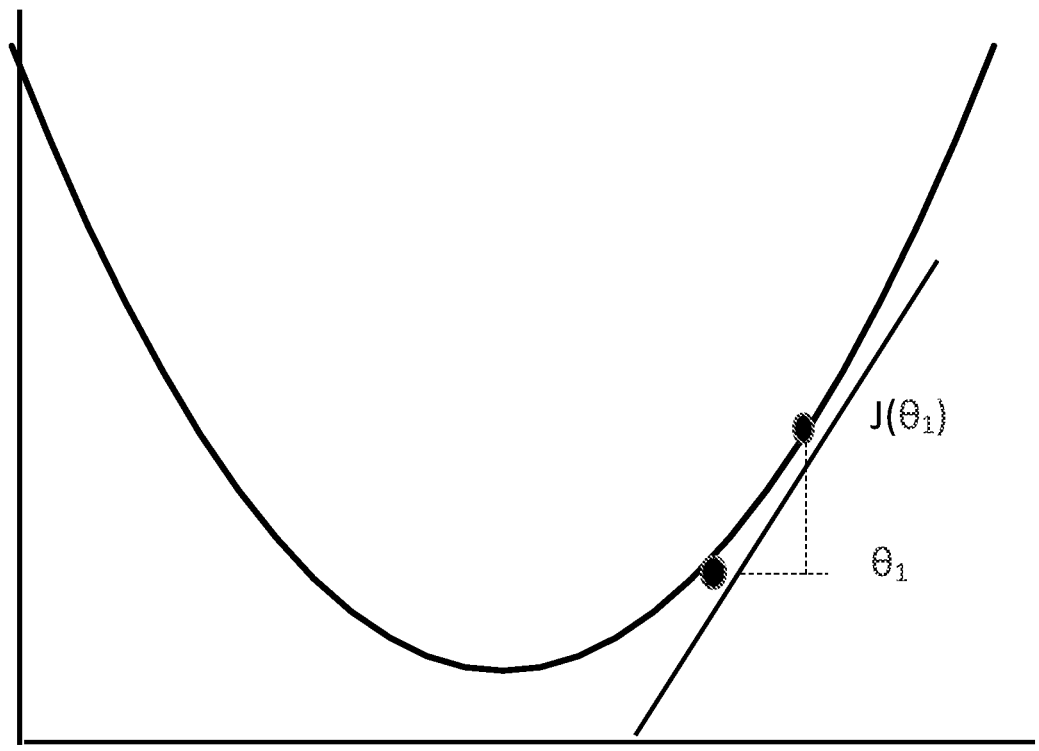
FIGS. 8 and 9 are plots of gradient descent.
Figure 9:
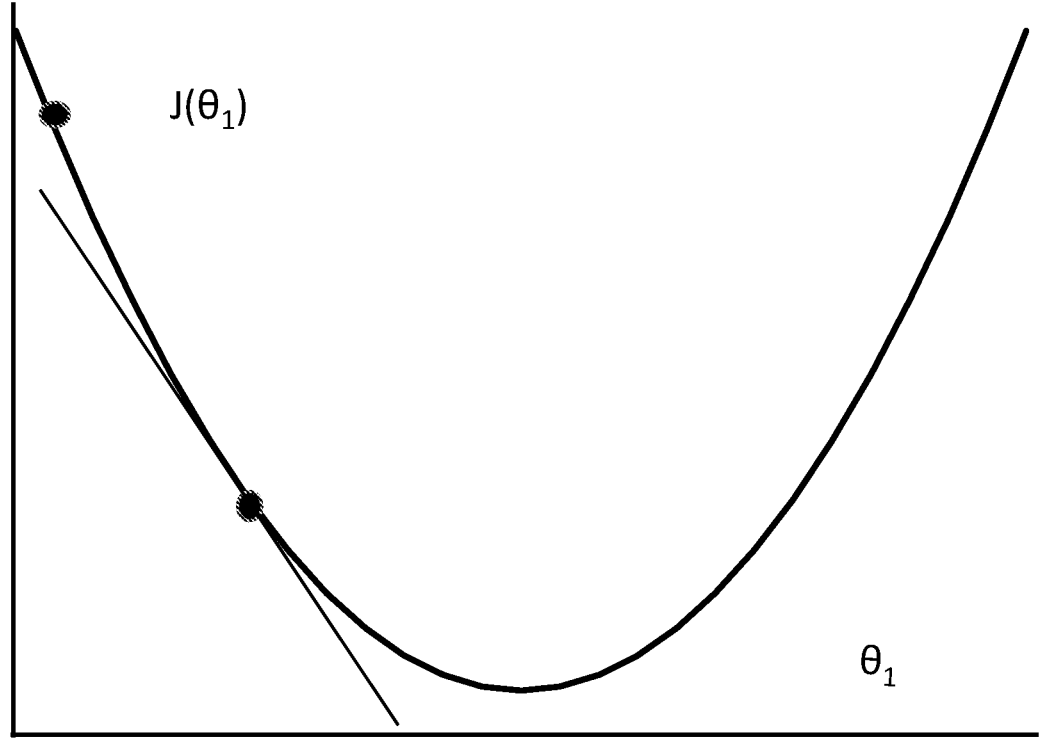

Let's see how it works if there is only one variable $\theta_1$ and $\theta_1 \in \mathbb{R}$:

$$\theta_1 = \theta_1 - \alpha \frac{\partial}{\partial \theta_1} J(\theta_1)$$

let us have a look at the partial derivative:

$$\beta = \alpha \frac{\partial}{\partial \theta_1} J(\theta_1)$$

if the derivative is positive as shown in FIG. 8
we are moving left:

$$\theta_1 = \theta_1 - \beta$$

if the derivative is negative as shown in FIG. 9
We are moving right:

$$\theta_1 = \theta_1 + \beta$$

Figure 10:
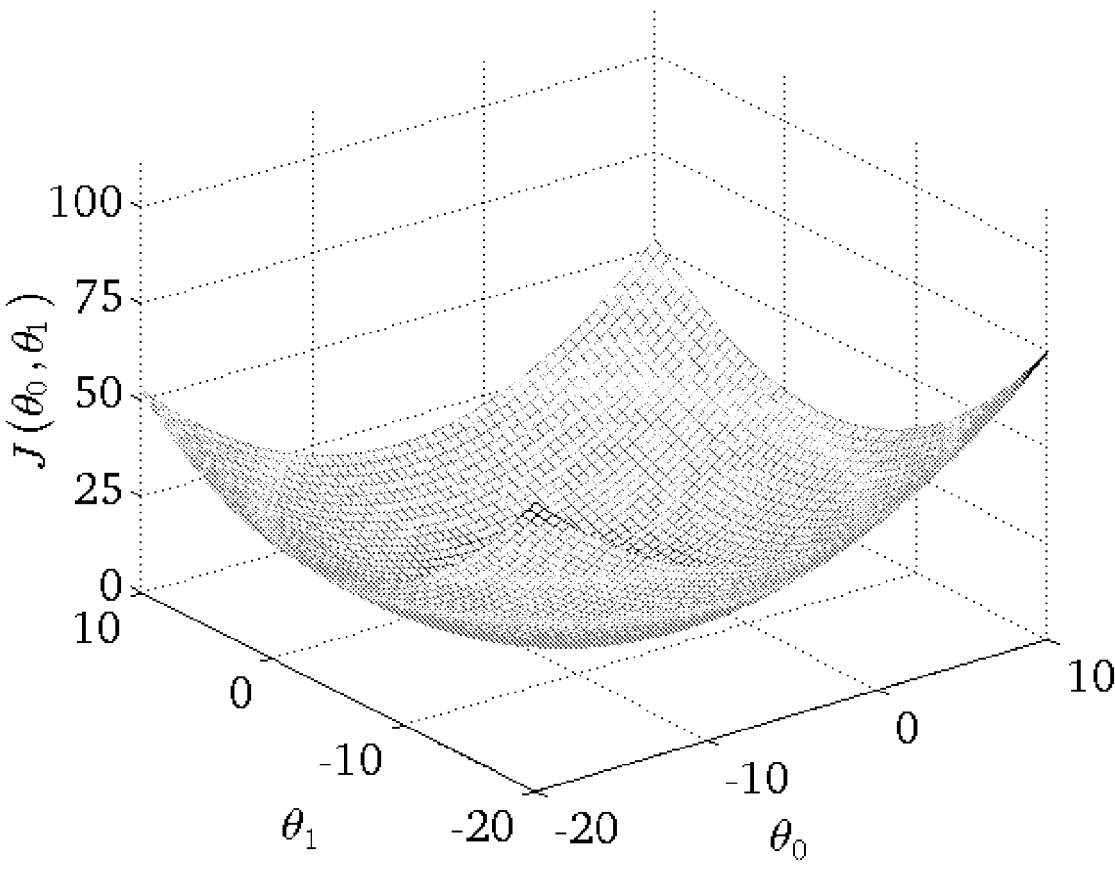
FIG. 10 is a plot for two variables of a cost function.

For two variables the cost function would look like that shown in FIG. 10;

Learning Rate
when $\alpha$ is too small—we are taking very small steps—too slow
when $\alpha$ is too large—we are taking too big steps and may miss the minimum
in this case not only may it fail to converge, but even diverge!

Approaching the Minimum
As we are approaching the local minimum, it takes smaller and smaller steps
If $\theta_1$ is at the local minimum, then $\beta = 0$ and $\theta_1$ will not change Convex Function
The cost function J must be convex if we do not want to end up in a local minimum.

Univariate Linear Regression
Given input data set $\{x^{(i)}, y^{(i)}\}$ of size m
We have our hypothesis $h(x) = \theta_0 + \theta_1 x$
how to choose $\theta_0$ and $\theta_1$ so $h(x)$ is closest to the set of input data We need to minimize the cost function:

$$j(\theta_1, \theta_2) = \frac{1}{2m} \sum_{i=1} m(h_0 x^{(i)} - y^{(i)})^2$$

This is the squared error cost function
Let us simplify our expression:

$$\frac{\partial}{\partial \theta_j} J(\theta_0, \theta_1) = \frac{\partial}{\partial \theta_j} \frac{1}{2m} \sum (h_\theta(x^i) - y^{(i)})^2 = \frac{\partial}{\partial \theta_j} \frac{1}{2m} \sum (\theta_0 + \theta_1 x^i - y^{(i)})^2$$

Now we calculate the derivatives and have:
for $\theta_0$:

$$\frac{\partial}{\partial \theta_0} J(\theta_0, \theta_1) = \frac{1}{m} \sum (h_\theta(x^{(i)}) - y^{(i)})$$

for $\theta_1$:

$$\frac{\partial}{\partial \theta_1} J(\theta_0, \theta_1) = \frac{1}{m} \sum (h_\theta(x^{(i)}) - y^{(i)})$$

So for the regression the algorithm is
repeat until converges $$\theta_0 = \theta_0 - \alpha \frac{\partial}{\partial \theta_0} J(\theta_0, \theta_1) = \frac{1}{m} \sum (h_\theta(x^{(i)}) - y^{(i)})$$

$$\theta_1 = \theta_1 - \alpha \frac{\partial}{\partial \theta_1} J(\theta_0, \theta_1) = \frac{1}{m} \sum (h_\theta(x^{(i)}) - y^{(i)}) \times x^{(i)}$$

(update simultaneously)
The square error cost function is convex, so we always converge to the global minimum.

Gradient Descent for Multivariate Linear Regression
For Multivariate Linear Regression we have $x^{(i)} \in \mathbb{R}^{n+1} x^{(i)}$ and $\theta = \in \mathbb{R}^{n+1}$, where
n—is number of features
m—number of training examples
and $x_0^{(i)} = 1$ for all i (the slope)
So out cost function takes the following form:

$$J(\theta) = J(\theta_0, \dots, \theta_n) = \frac{1}{2m} \sum_{i=1}^{m} (h_\theta(x^{(i)}) - y^{(i)})^2$$

The algorithm:
repeat
simultaneously for all i $$\theta_j = \theta_j - \alpha \frac{\partial}{\partial \theta_j} J(\theta)$$

or, having calculated the derivatives:
repeat
simultaneously for all i $$\theta_j = \theta_j - \alpha \frac{1}{m} \sum (h_\theta)(x^{(i)}) - y^{(i)}) \times x_j^{(i)}$$

Gradient Descent in Practice

Feature Scaling

Use Feature Scaling to help GD converge faster

Learning Rate

How to choose α:

If gradient descent works properly, cost function should decrease after each iteration if J decreases by less than $\epsilon=10^{-3}$ in one iteration—declare convergence If J is increasing instead—need to make α smaller Choosing α:

But do not choose α too small—it will take too long to converge

To choose α try

. . . , 0.001, 0.01, 0.1 . . . or increase it 3-fold

And see what is acceptable

Figure 2:
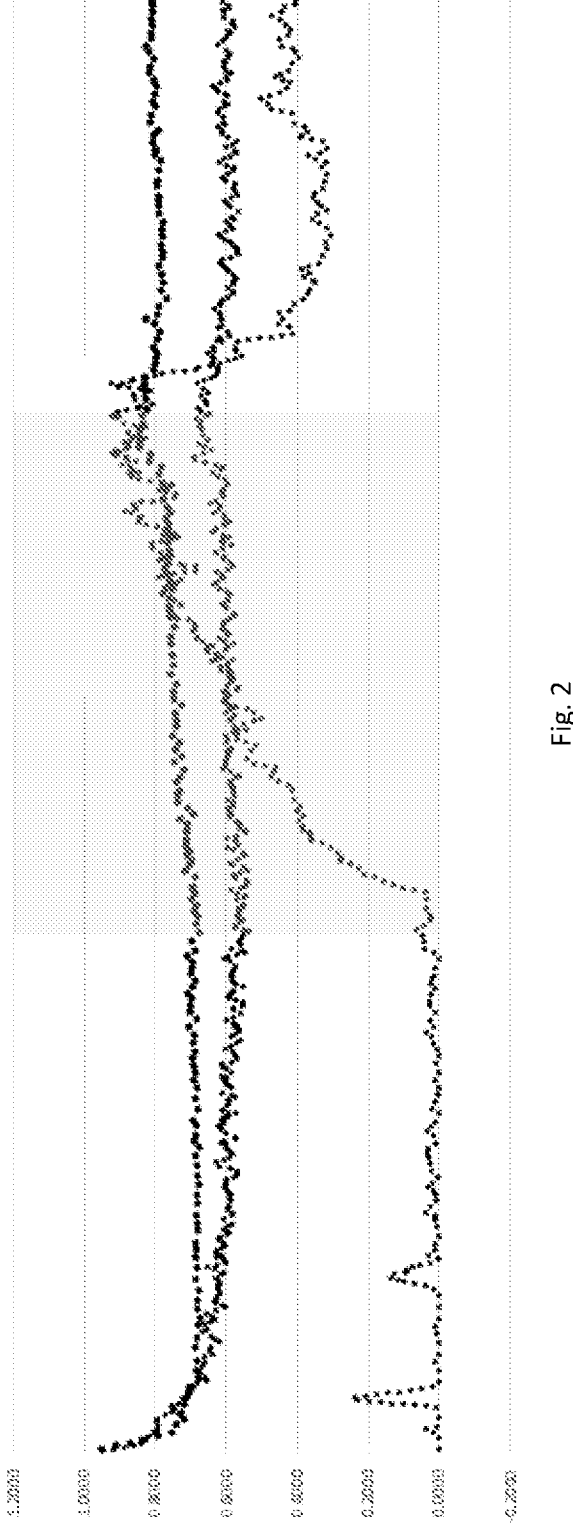
FIG. 2 is an illustrative graph of a collection of raw data points from each of three sensor means.

FIG. 2 illustrates the recording of raw sensor means data recorded every second. The highlighted (gray) area designates when a negative odor is present (by subjective "smell" test) in the surrounding environment (in this instance a residential bathroom). The goal is to have an algorithm correctly determine when a negative odor is present in the environment. Three sensor means were used as follows:

CCS8811 Air Quality Sensor from Adafruit

SainSmart MQ135 Sensor for ammonia

SainSmart MQ136 Hydrogen Sulfide Sensor

Figure 3:
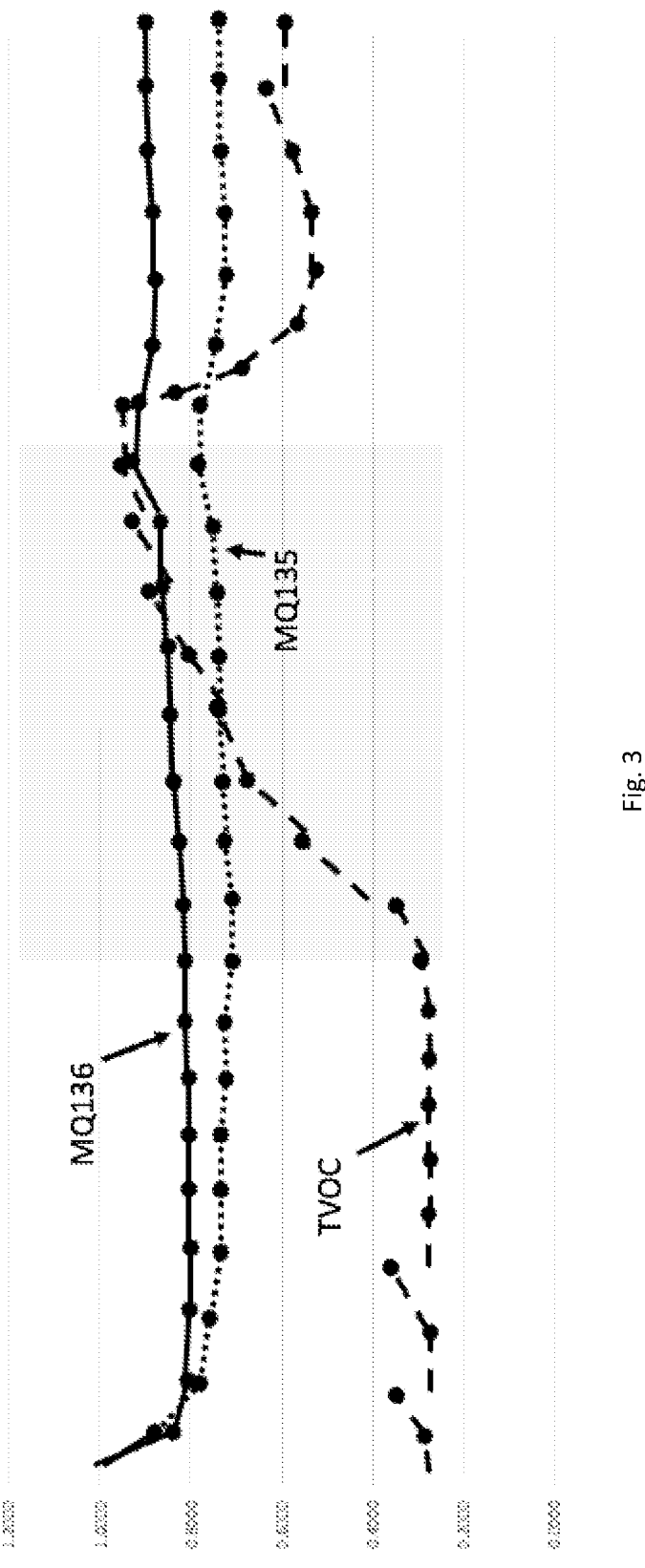
FIG. 3 is an illustrative graph of a linear least squares regression for each of three sensor means data performed continuously over 20 data points.

FIG. 3 is an illustrative example of a training data set. As already noted, FIG. 3 illustrates a linear regression performed for the raw data of FIG. 2 continuously over 20 data points for each of three (3) sensor means. As shown, this results in three different data points at any given time, the slopes of each regression line. The number of data points for each sensor means can vary, for example about 5 to about 500. As shown, the data points are collected every second, but could vary, for example, between about 0.1 and about 10 seconds. What designates this data set as training data is the fact is that it is labeled. That is for each set of inputs (sensor means values) there is a stated output (whether an odor is present). In FIG. 3 the area where an odor is detected by a human is highlighted in gray.

Figure 4:
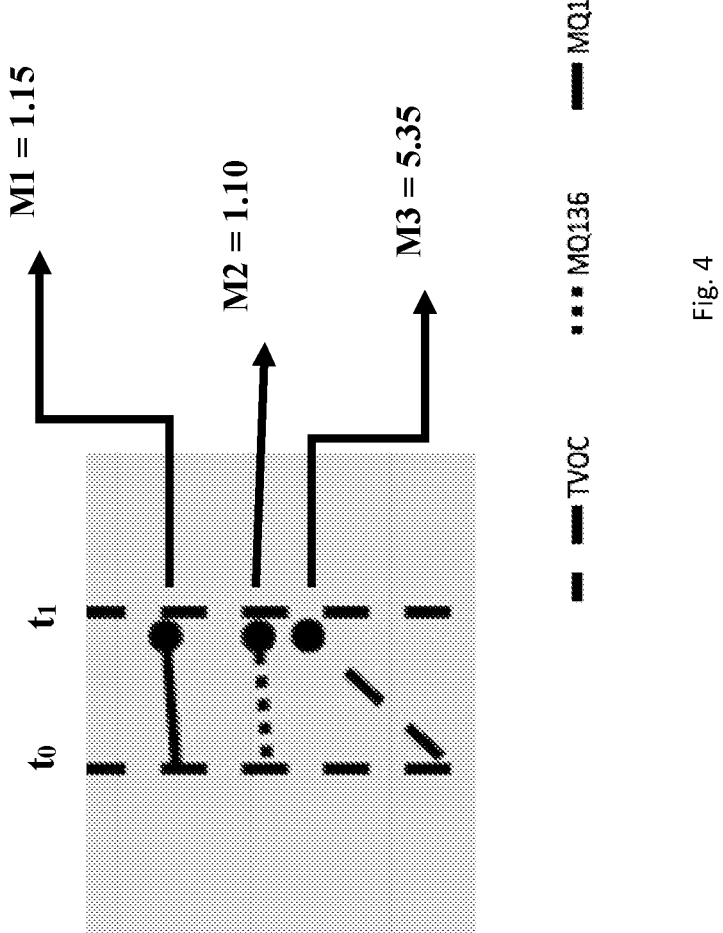
FIG. 4 is an expanded view of linear least square regression lines between times $t_0$ and $t_1$ labeled with their associated slopes.
Figure 5:
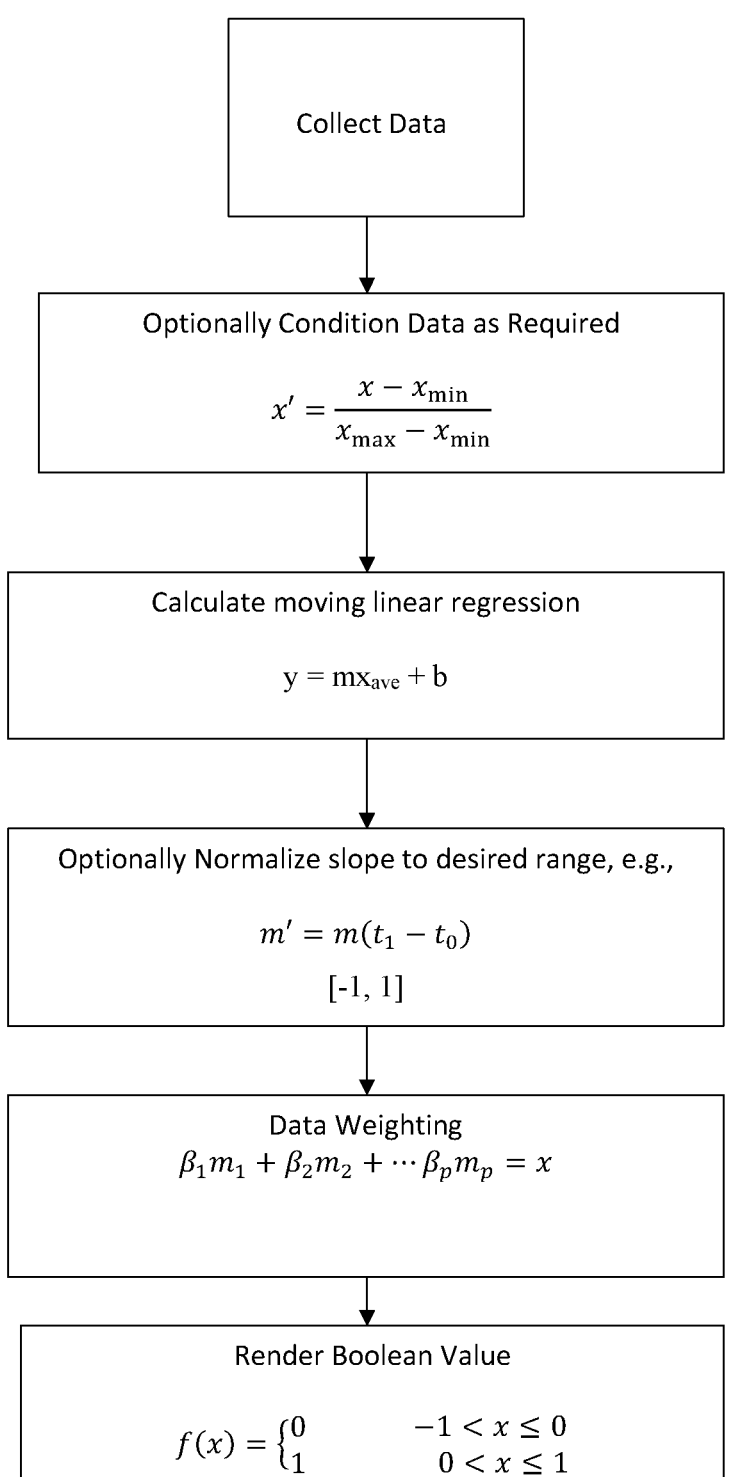
FIG. 5 is a flow chart illustrating the algorithm steps described hereinbelow.

FIG. 4 shows an expanded view of a randomly chosen segment from FIG. 3 (from $t_0$-$t_1$) with the slopes of each sensor means indicated as determined by linear least squares regression. Thus, the slope $(m_1)$ for sensor means MQ135 was determined to be 1.15 (M1), the slope $(m_2)$ for sensor means MQ136 was determined to be 1.10 (M2) and the slope $(m_3)$ for sensor means CCS8811 was determined to be 5.35 (M3).

Each of the slopes is then fed into the inferred function using equation (9) above. The supervised machine learning process produces an inferred function which is then used for mapping new examples. For 3 sensor means, according to equation (8), the inferred function is:

$$\beta_1 m_1 + \beta_2 m_2 + \beta_3 m_3 = x, \qquad (11)$$

Where β is the weighting factor for weighting the respective slopes. Substituting the slopes shown in FIG. 4, into this equation yields:

$$\beta_1 1.15 + \beta_2 1.10 + \beta_3 5.35 = x \qquad (12)$$

and the Boolean function according to equation (9) is:

$$f(x) = \begin{cases} 0 & x \le 1 \\ 1 & 1 < x \end{cases}$$

The inferred function yields a value for x that is then fed into the Boolean function. The x values that will trigger spray or no spray can be chosen randomly. For example, if the value is less than or equal to 1 the function returns a 0 (don't spray), and if the value for x is greater than 1 the function returns a 1 (spray).

With reference again to FIG. 3, the slopes of the three sensor readings are known, all of which are in the highlighted, odor sensed zone thereof. Values of $\beta_1$) $\beta_2$ and $\beta_3$ are sought that render a Boolean function result of X>1. starting with a guess for these values and refining using multivariant multiple descent, values are found that render the correct Boolean function, which is X>1. Performing this process multiple times with known slopes, both falling withing the highlighted area (odor sensed) and outside thereof (no odor sensed), an inferred function is derived for mapping new readings from the sensors using gradient descent.

The invention claimed is:

1. A method comprising:

a. exposing at least one sensor means to a surrounding environment for detecting and responding to the presence of at least one odor causing agent, b. periodically converting the response of each sensor means to a periodic electrical output signal, c. sending each periodic electrical output signal to control means wherein a plurality of periodic electrical output signals are used to calculate by linear least squares regression the slope between the periodic electrical output signals, d. adding the slopes e. activating expulsion of an odor treatment agent into the surrounding environment when the added slopes of all sensor means exceeds a threshold level.

2. The method of claim 1, wherein a plurality of target odor causing agent compositions in the surrounding environment are detected, wherein the responses are converted to electrical output signals for each target odor causing agent composition that vary according to variations in the presence of each output signal, wherein a plurality of successive data points reflecting the electrical output signals are processed for each target odor causing agent composition detected to periodically estimate the slope of a line therethrough by linear least squares regression, and wherein the estimated slopes are added together.

3. The method of claim 2, wherein the respective slopes are weighted before being added together.

4. The method of claim 2, wherein the respective slopes are weighted before being added together using weighting factors determined by gradient descent.

5. The method of claim 2, wherein a first odor causing agent composition is detected and a second odor causing agent composition excluding the first odor causing agent composition is detected.

6. The method of claim 3, wherein a first odor causing agent composition is detected and a second odor causing agent composition excluding the first odor causing agent composition is detected.

7. The method of claim 2, wherein a third odor causing agent is detected excluding a first odor causing agent composition, and a second odor causing agent composition is detected excluding the first odor causing agent composition and the third odor causing agent composition.

8. The method of claim 3, wherein a third odor causing agent is detected excluding a first odor causing agent composition, and a second odor causing agent composition is detected excluding the first odor causing agent composition and the third odor causing agent composition.

9. The method of claim 2, wherein the data points for each odor causing agent composition are processed to periodically estimate the slope of a line therethrough by moving linear least squares regression.

10. The method of claim 3, wherein the data points for each odor causing agent composition are processed to periodically estimate the slope of a line therethrough by moving linear least squares regression.

5

* * * * *